United States Patent
Hasegawa et al.

(10) Patent No.: US 9,339,255 B2
(45) Date of Patent: May 17, 2016

(54) ULTRASONIC PROBE

(75) Inventors: Shigeyoshi Hasegawa, Tsukui-gun (JP); Kazuyoshi Irioka, Sagamihara (JP); Jun Koizumi, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 795 days.

(21) Appl. No.: 13/164,160

(22) Filed: Jun. 20, 2011

(65) Prior Publication Data

US 2011/0245681 A1 Oct. 6, 2011

Related U.S. Application Data

(62) Division of application No. 10/513,196, filed as application No. PCT/JP03/11170 on Sep. 1, 2003, now abandoned.

(30) Foreign Application Priority Data

Sep. 2, 2002 (JP) .................. 2002-256984

(51) Int. Cl.
*A61B 8/00* (2006.01)
*A61B 8/12* (2006.01)
*G10K 11/00* (2006.01)
*G10K 11/35* (2006.01)

(52) U.S. Cl.
CPC ............... *A61B 8/12* (2013.01); *A61B 8/4461* (2013.01); *G10K 11/004* (2013.01); *G10K 11/355* (2013.01)

(58) Field of Classification Search
CPC ...... A61B 8/12; A61B 8/4461; G10K 11/004; G10K 11/355

USPC .............................................. 600/459; 73/584
See application file for complete search history.

(56) References Cited

U.S. PATENT DOCUMENTS

| 5,085,221 | A | 2/1992 | Ingebrigtsen et al. |
| 5,176,142 | A * | 1/1993 | Mason ........................ 600/463 |
| 5,460,179 | A | 10/1995 | Okunuki et al. |
| 5,513,639 | A | 5/1996 | Satomi et al. |
| 6,213,948 | B1 | 4/2001 | Barthe et al. |
| 2002/0045381 | A1 | 4/2002 | Ishii et al. |
| 2002/0060508 | A1 | 5/2002 | Sudol et al. |
| 2002/0084456 | A1 | 7/2002 | Sugihara et al. |
| 2002/0115312 | A1 * | 8/2002 | Matsuzaki et al. .............. 439/15 |
| 2003/0168945 | A1 | 9/2003 | Birgel |

FOREIGN PATENT DOCUMENTS

| EP | 0 571 992 | 1/1993 |
| JP | 59-124355 | 8/1984 |
| JP | 59-124357 | 8/1984 |

(Continued)

*Primary Examiner* — Jonathan Cwern
(74) *Attorney, Agent, or Firm* — Lucas & Mercanti, LLP

(57) ABSTRACT

In an ultrasonic probe including an element part 1 for transmitting and receiving ultrasonic waves, a relay cable 2 connected to the element part 1 and an oscillation mechanism part for oscillating the element part, a cross section of the relay cable 2, which is taken perpendicularly to a rotation axis 3 of the oscillation that is provided to the element part 1 by the oscillation mechanism part, has at least two arc-shaped parts smoothly connected each other, more specifically, S-shape arc-shaped parts or reversed S-shaped parts. In addition, the relay cable 2 is drawn from the surface of the element part 1 facing the rotation axis 3. In this manner, the stress applied to the relay cable 2 during the oscillation of the element part 1 can be dispersed, thereby improving durability of the relay cable 2.

11 Claims, 4 Drawing Sheets

(56) References Cited

FOREIGN PATENT DOCUMENTS

| JP | 62-140451 | 9/1987 |
|----|-----------|--------|
| JP | 04258854 A | 9/1992 |
| JP | 5-13408 | 2/1993 |
| JP | 6-038962 | 2/1994 |
| JP | 6-335481 | 12/1994 |
| JP | 5-23339 | 2/2003 |
| WO | WO 97/23865 | 7/1997 |

* cited by examiner

ULTRASONIC PROBE

This application is a division of U.S. application Ser. No. 10/513,196, filed on Nov. 2, 2004, which is a U.S. National Stage application of International Application No. PCT/JP2003/011170, filed Sep. 1, 2003, which application is incorporated herein by reference.

TECHNICAL FIELD

The present invention relates to an ultrasonic probe, more specifically, an ultrasonic probe having a relay cable that is used for drawing a signal line and has improved durability.

BACKGROUND ART

A known ultrasonic probe used for an ultrasonic diagnostic apparatus has an ultrasonic element for transmitting and receiving ultrasonic waves, and oscillates the ultrasonic element in a housing part filled with an acoustical coupling medium. The acoustical coupling medium has an acoustic impedance similar to that of living organisms. Such an ultrasonic probe is, for example, described in JP 6(1994)-038962A.

FIG. 5 is a cross-sectional view of the configuration of a conventional ultrasonic probe. The ultrasonic probe 20 is connected to an ultrasonic diagnostic apparatus (not shown in the figure) via a cable 25. The ultrasonic probe 20 has a housing 21 that is composed of an upper case 22 and a lower case 24 and includes a partitioning film 23 therein. In the space enclosed by the partitioning film 23 and the lower case 24, an acoustical coupling medium 27 is sealed. In the housing 21, an element part 26 is provided so that a portion for transmitting and receiving ultrasonic waves can be set in the acoustical coupling medium 27. In addition, an oscillation mechanism part 29 is equipped in the housing 21 for oscillating the element part 26. As shown in the figure, a rotation center 28 for the oscillation of the element part 21 is positioned at the center of a living organism contact barrier 24A forming an apex of the lower case 24. Moreover, a relay cable (not show in the figure) is connected to the element part 26 so as to draw a signal line from the element part 26. The relay cable is electrically connected to a cable 25, and signals received by the element part 26 can be input into the ultrasonic diagnostic apparatus via the cable. In the conventional ultrasonic probe, however, the relay cable is positioned at a distance from the central axis of the oscillation of the element part, leading to problems such as the incremental change in the drawing length of the relay cable and frequent bending and breaking of the relay cable with the oscillation of the element part.

DISCLOSURE OF THE INVENTION

In light of the above-stated conventional problems, it is an object of the present invention to provide an ultrasonic probe that can suppress the bending and the breaking of a relay cable drawing a signal line from an ultrasonic element part at the time of oscillation of the element part.

In order to attain the above-mentioned object, an ultrasonic probe of the present invention includes an element part for transmitting and receiving ultrasonic waves, a relay cable connected to the element part and an oscillation mechanism part for oscillating the element part, wherein a cross section of the relay cable, that is taken perpendicularly to a rotation axis of the oscillation provided to the element part by the oscillation mechanism part, has at least two arc-shaped parts smoothly connected each other.

BEST MODE FOR CARRYING OUT THE INVENTION

Figure 1:
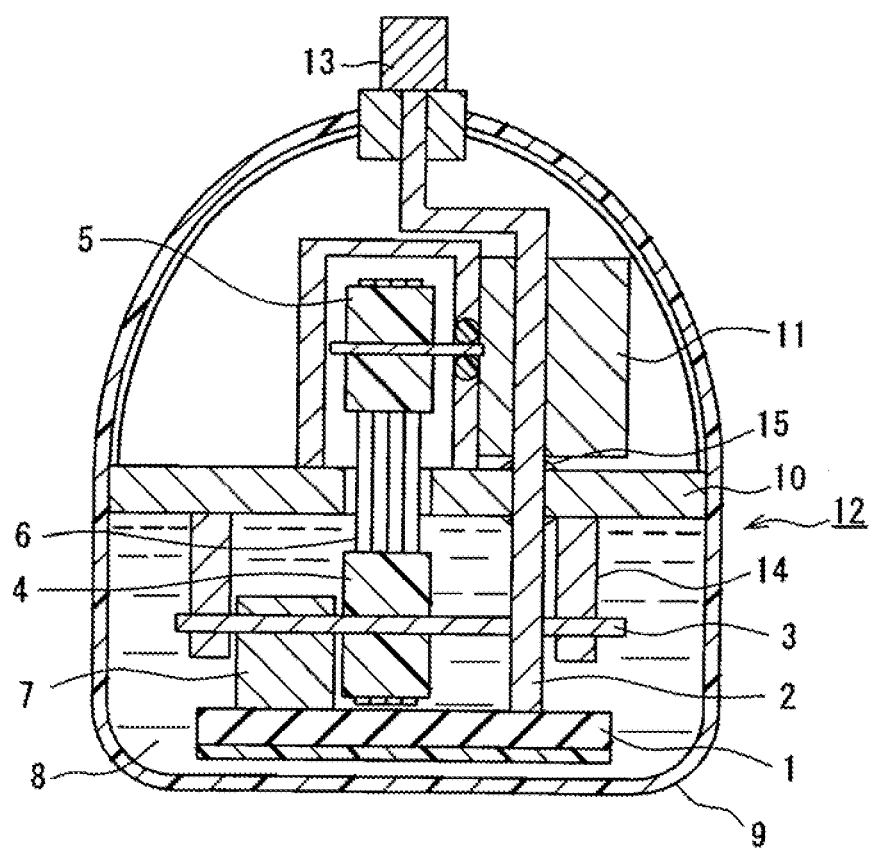
FIG. 1 is a cross-sectional view of an example of an ultrasonic probe according to Embodiment 1 of the present invention.

As mentioned above, an ultrasonic probe of the present invention includes an element part for transmitting and receiving ultrasonic waves, a relay cable connected to the element part and an oscillation mechanism part for oscillating the element part, wherein a cross section of the relay cable, that is taken perpendicularly to a rotation axis of the oscillation provided to the element part by the oscillation mechanism part, has at least two arc-shaped parts smoothly connected each other.

In the above-mentioned configuration, a mechanical load that is applied to the relay cable during the oscillation of the element part is dispersed, thus stress concentration can be suppressed, thereby preventing bending and breaking of the relay cable.

It is preferable that, in the ultrasonic probe, the cross section of the relay cable perpendicular to the rotation axis has two arc-shaped parts positioned point-symmetrically about an assumed point and shaped similarly to each other. More specifically, the cross section perpendicular to the rotation axis preferably has a S-shape or a reversed S-shape.

Moreover, in the ultrasonic probe, the relay cable is preferably drawn from the surface of the element part at the side of the rotation axis. More preferably, the rotation axis is located at or around the curvature center of one of the arc-shaped parts that compose a cross section of the relay cable perpendicular to the rotation axis. In this preferred example, by drawing the relay cable toward the rotation axis, it is possible to decrease the operation range of the relay cable during its oscillation, thereby decreasing the mechanical distortion applied to the cable.

Additionally, in the ultrasonic probe, at least a part of the relay cable preferably is structured as a laminate of plural flexible printed board or plural flexible flat cables. In this preferred example, the relay cable can be decreased in the thickness and prevented from distortion due to its bending. Furthermore, multiple signal lines can be connected to the relay cable by using such a laminate including two or more layers.

Here, in the ultrasonic probe, the plural flexible printed boards or the plural flexible flat cables preferably are laminated in a state being in contact but not fixed with each other.

In addition, in the ultrasonic probe, the flexible printed boards or the flexible flat cables preferably have signal lines formed on the one sides and ground lines formed on the other sides.

Furthermore, in the ultrasonic probe, the element part preferably includes an array element formed by arraying plural oscillators, and the flexible printed boards or the flexible flat cables preferably have plural signal lines corresponding respectively to the oscillators.

Still further, it is preferable that the plural oscillators are divided into some groups, and received signals of the oscillators are processed for each of the groups. It is preferable that the flexible printed boards or the flexible flat cables have plural signal lines corresponding respectively to the oscillators, and the signal lines are bound together for each of the groups.

The following is a description of the embodiments of the present invention with reference to the accompanying drawings.

Embodiment 1

FIG. 1 is a cross-sectional view of an example of the ultrasonic probe according to Embodiment 1 of the present invention. The ultrasonic probe can be connected to an ultrasonic diagnostic apparatus (not shown in the figure) by a cable 13 drawn from the interior of the probe.

In the ultrasonic probe, a housing part 12 is formed by joining a frame 10 to a window 9. A degassed acoustical coupling medium 8 is filled in the housing part 12.

The housing part 12 further includes an ultrasonic element unit, and the ultrasonic element unit has an element part 1 for transmitting and receiving ultrasonic waves. The element part 1 includes oscillators composed of a piezoelectric material such as a piezoelectric ceramic. For the element part 1, an array element formed by arraying plural oscillators can be used. The number of the oscillators composing the array element is not particularly limited, but it is, for example, 32 or 64.

Furthermore, the ultrasonic element unit includes a supporting plate 7 that supports the element part 1, and a rotation axis 3 that supports the supporting plate 7. The rotation axis 3 is supported rotatably by a bearing 14 attached to the frame 10. Accordingly, the element part 1 fixed to the supporting plate 7 can oscillate in synchronization with the rotation of the rotation axis 3.

The ultrasonic probe further includes an oscillation mechanism part for oscillating the ultrasonic element unit. The oscillation mechanism part includes a motor 11 for generating driving forces, a driving pulley 5 attached to an output shaft of the motor 11, a driven pulley 4 attached to the rotation axis 3 of the ultrasonic element unit and a belt 6 bridged between the pulleys 4 and 5. In the oscillation mechanism part, a driving force of the motor 11 can be transferred to the driven pulley 4 through the belt 6, and the element part 1 of the ultrasonic element unit can rotate together with the driven pulley 4. Here, by reversing the rotating direction of the motor 11 from alternately, the element part 1 can oscillate instead of rotating.

Furthermore, the relay cable 2 is connected to the element part 1 of the ultrasonic element unit. The relay cable 2 has a function of drawing out plural signal lines for the transmission and reception of electric signals from the element part 1. Preferably, the relay cable 2 is drawn out from a surface of the element part 1 facing the rotation axis 3 (upper surface of the element part 1 in the example illustrated in FIG. 2). The relay cable can be connected to the element part 1 by using a presser plate or the like.

In addition, the relay cable 2 passes through the frame 10 and is electrically connected to a cable 13. Generally, this relay cable 2 is fixed firmly to the frame 10 at the part of passing-through. The fixation to the frame 10 is carried out using an adhesive 15 in a fluid-tight manner for preventing leakage of the acoustical coupling medium 8.

For the relay cable 2, a flexible cable (e.g., high-density OKIFLEX (trade name) manufactured by Oki Electric Cable Co., Ltd.) can be used.

Figure 2:
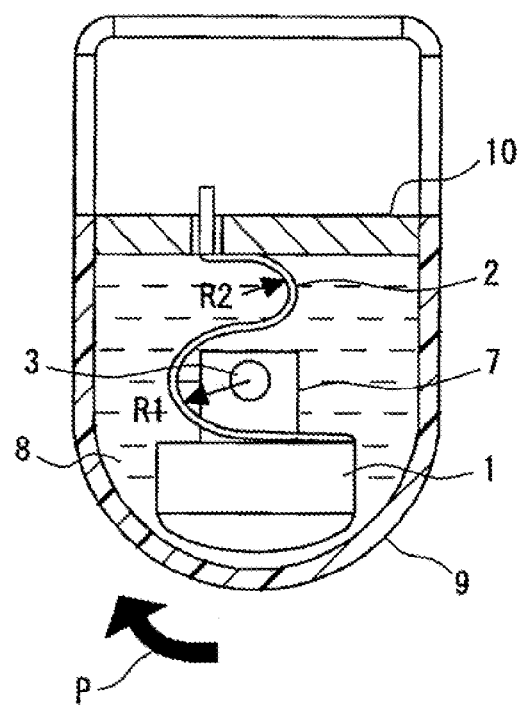
FIG. 2 is a partial cross-sectional view of the configuration of the ultrasonic probe.

FIG. 2 is a cross-sectional view of the ultrasonic probe, which is taken perpendicularly with respect to the rotation axis 3. FIG. 2 assigns the same parts with the same reference numerals as FIG. 1. As illustrated in FIG. 2, the relay cable 2 is arranged so that its cross section perpendicular to the rotation axis 3 can have two arc-shaped parts smoothly-connected each other. In addition, the relay cable 2 is also arranged so that the rotation axis 3 can be positioned at the curvature center of one of the arc-shaped parts (hereinafter, the arc-shaped part at which the rotation axis 3 is located will be called "a first arc-shaped part", and the other arc will be called 2 "a second arc-shaped part").

In the present embodiment, the two arc-shaped parts are positioned point-symmetrically about an assumed point, and regarded as having similar figures. More specifically, the cross section of the relay cable 2 is S-shaped or reversed S-shaped. In the relay cable 2, an angle of each arc-shaped part (an angle formed by straight lines linking the curvature center and the both ends of the arc) is preferable 180° or larger, that is, each arc-shaped part makes a part not smaller than a semicircle so as to prevent sharp bending in the relay cable 2.

It is also preferable that the arc-shaped parts of the relay cable 2 respectively start from a point fixed to the frame 10 and from a point connected to the element part 1. It is further preferable that, at the point fixed to the frame 10 and the point connected to the element part 1, the relay cable 2 extends in the direction substantially parallel to the surface of the frame 10 or to the surface of the element part 1.

Next, the operation of the ultrasonic probe is described with reference to FIG. 1 and FIG. 2.

First, the oscillation mechanism part is driven to oscillate the element part 1 of the ultrasonic element unit. Then, an electric signal (a transmission signal) is transmitted to the element part 1, converted into ultrasonic waves at the element part 1. The ultrasonic waves are conveyed in the acoustical coupling medium 8, and transmitted from the window 9 to an object. The thus transmitted ultrasonic waves are reflected by the object, and a part of the reflected waves is received by the element part 1 and then converted into an electric signal (a received signal). The received signal passes through the relay cable 2 and the cable 13, and subsequently passes through the relay substrate (not shown in the figures) as appropriate, so as to be input into an ultrasonic diagnostic apparatus (not shown in the figures) that has a signal processing circuit.

When the element part 1 is oscillated by the mechanism part, the relay cable 2 bends and stretches alternately, while changing the curvature of the arcs, so as to correspond to the oscillation of the element part.

FIG. 2 illustrates the element part positioned at the middle of the scanning range. In FIG. 2, R1 and R2 denote the radiuses of the first arc-shaped part and the second arc-shaped part, respectively. When the element part 1 is moved by the oscillation mechanism part from this position in the direction shown by an arrow P, the first arc-shaped part is deformed to increase its radius R1, and second arc-shaped part is deformed to decrease its radius R2. When the element part 1 is moved in the reverse direction to the arrow P, the first arc-shaped part and the second arc-shaped part are deformed respectively to decrease the R1 and to increase the R2. Due to the deformation, the relay cable 2 will be applied with mechanical load over the entire arc-shaped parts. Here, since the movement of the element part 1 is not a rotation but an oscillation, winding or tension of the relay cable 2 does not occur in general.

As mentioned above, according to Embodiment 1 of the present invention, repeated stresses applied to the relay cable are dispersed, thereby decreasing the fatigue of the metal conductor of the relay cable so as to suppress failures such as breaking, thus providing an apparatus with improved stability. In addition, according to the present embodiment, the range of the cable's movement caused by oscillation is decreased to reduce the length and the moving space of the relay cable, and thus a more compact apparatus can be obtained.

Embodiment 2

Figure 3:
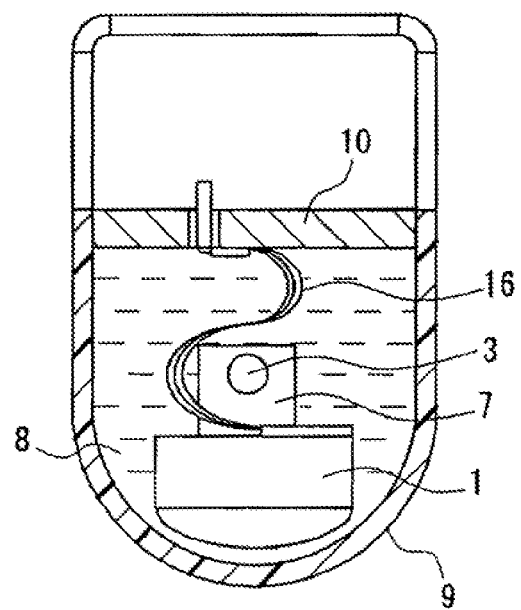
FIG. 3 is a cross-sectional view of an example of the ultrasonic probe according to Embodiment 2 of the present invention.

FIG. 3 is a cross-sectional view of an example of the ultrasonic probe according to Embodiment 2 of the present invention. Similarly to FIG. 2, this figure is a cross section taken perpendicularly to the rotation axis of the element part of the ultrasonic probe. Here, FIG. 3 assigns the same parts with the same reference numerals as FIG. 1 and FIG. 2.

In the ultrasonic probe, a part of the relay cable 16 is formed by laminating plural flexible printed boards or flexible flat cables. In the laminated part, the layers are in contact with each other but physically separate so as not to be fixed to each other. The number of the layers to be laminated is not limited particularly but may be, for example, from 3 to 5.

For the flexible printed board, for example, FLEXIBLES CIRCUIT (trade name) manufactured by NOK CORPORATION can be used. For the flexible flat cable, for example, LEAFCONN (trade name) manufactured by Shibata Corporation Ltd. can be used.

Except for the above-mentioned structures, the ultrasonic probe of the present embodiment is substantially the same as that of Embodiment 1. The operations and the effects are also similar to those in Embodiment 1.

According to the present embodiment, multiple connections can be provided by using a laminate of flexible printed boards or flexible flat cables for the relay cable. Since the ends of the flexible printed boards or the flexible flat cables for the relay cable are fixed respectively to the element part and the frame, twisting and waving during the oscillation of the element part can be prevented. Thereby, disorder of the scanning traces of the element part, which may be caused by twisting or the like of the relay cable, can be suppressed to secure a stable operation.

Embodiment 3

Figure 4:
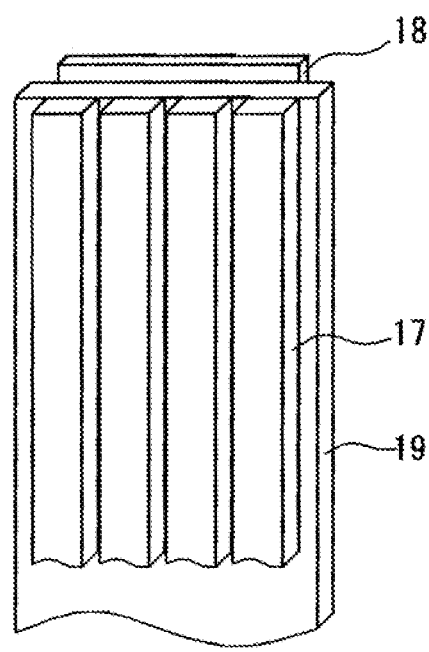
FIG. 4 is a perspective view of an example of a flexible printed board composing the ultrasonic probe.
Figure 5:
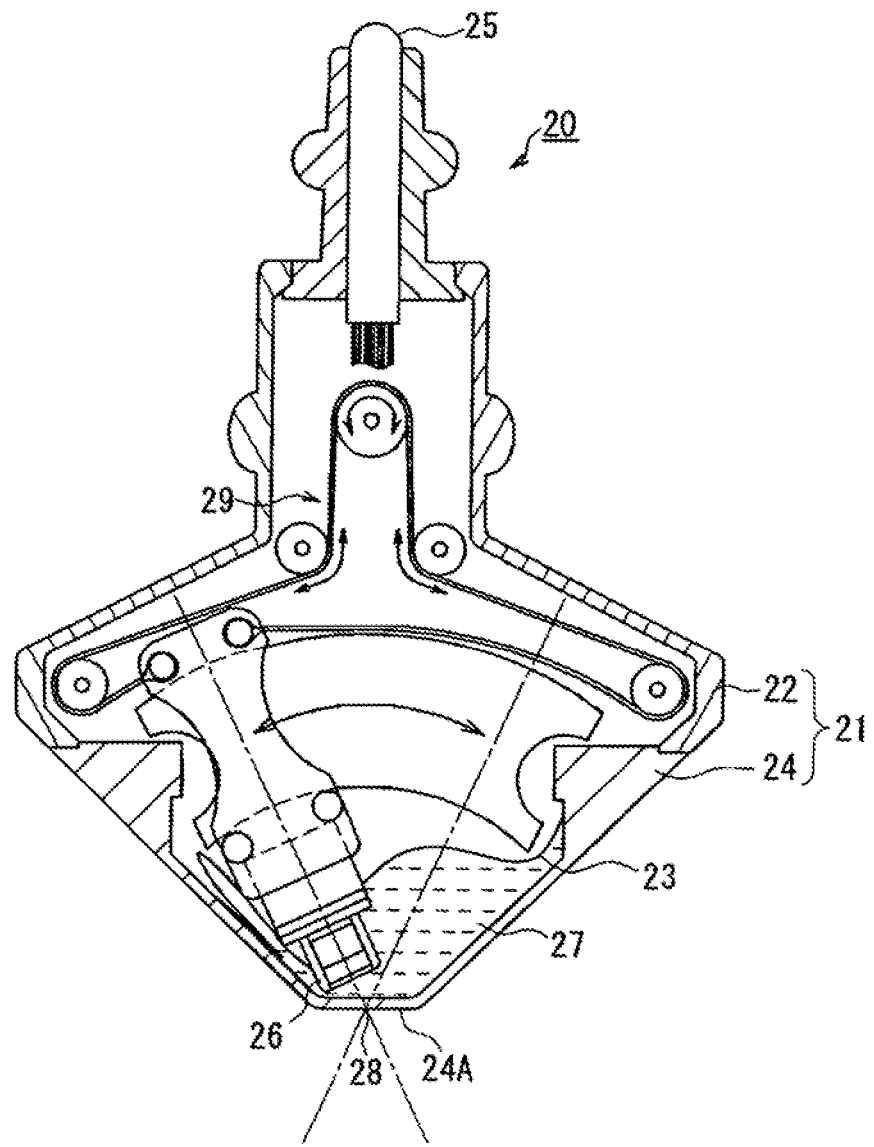
FIG. 5 is a cross-sectional view of a conventional ultrasonic probe.

FIG. 4 is a perspective view of an example of a flexible printed board that can be used for the relay cable in Embodiment 2.

The flexible printed board includes a substrate 19, signal line pattern 17 formed on one surface of the substrate 19 and a ground pattern 18 formed on the other surface of the same substrate 19. The substrate 19 is composed of a material that has sufficient strength even when it is thinned, such as polyimide and polyester. For the signal line pattern 17 and the ground pattern 18, a conductive material such as a metal like Cu is used. The conductive parts on the both surfaces of the flexible printed board preferably are coated with an insulating material by an overlay processing.

Use of the above flexible printed board enables protection of the signal lines from noises, and decreases the cross talk between the signal lines.

In the flexible printed board, the number of the signal line patterns 17 is preferably the same as that of driving channels, that is, the number of oscillators composing the element part.

In some methods of driving the ultrasonic diagnostic apparatus, the oscillators are divided into some groups, and received signals of the oscillators are processed for each of the groups. In the above methods, the plural signal line patterns 17 formed on the flexible printed board, which correspond respectively to the oscillators, are preferably bound together for each of the above-mentioned groups.

According to the above-described structure, a layout of connector pins can be recognized easily when connecting the flexible printed boards to the array elements, and this can decrease wiring errors and facilitate checkups. Moreover, this structure also allows simplified wiring, and decreases harmful effects such as interference occurring between the oscillators.

Although the above description is regarding the flexible printed boards, it is substantially applicable to the flexible flat cables as well.

The example illustrated in FIG. 4 relates to a flexible printed board that can be applied when the element part is composed of linear array type elements. However, the present invention is not limited to the example. It is also substantially applicable, for example, to the structure that the element part includes convex type elements.

In any of the embodiments, the scanning method using ultrasonic waves is not particularly limited, and can be applied to ultrasonic probes or the like regarding electric sector scanning or mechanical sector scanning.

INDUSTRIAL APPLICABILITY

As mentioned above, the ultrasonic probe of the present invention enables to dispersion of the mechanical load that is applied to the relay cable during the oscillation of the element part, and prevent the relay cable from bending and breaking, thereby providing an apparatus with high reliability. The ultrasonic probe is particularly useful for the ultrasonic diagnostic apparatus which obtains information about the interior of a living organism by transmitting and receiving ultrasonic waves with respect to the living organism.

The invention claimed is:
1. An ultrasonic probe comprising:
an element part for transmitting and receiving ultrasonic waves;
a relay cable connected to the element part, for transmitting a signal to the element part;
liquid for transmitting ultrasonic waves;
a frame and a window constituting a housing part in which the element part and the relay cable are housed, the liquid being sealed inside the housing part; and
an oscillation mechanism part for oscillating the element part,
wherein the oscillation mechanism part has a rotation axis configured to provide oscillation movement of the element part and a supporting plate that connects the rotation axis and the element part,
the relay cable has a S-shape or a reversed S-shape with two arc-shaped parts in a plane perpendicular to the rotation axis,
one end of the relay cable is connected to a cable connecting surface of the element part facing the rotation axis and, when the element part is positioned at a middle of a scanning range, in a connected portion with the element part, the relay cable is drawn from a point connected to the element part in a direction substantially parallel to the cable connecting surface, the rotation axis is located at a curvature center of at least one of the arc-shaped parts, a part of a side face of the rotation axis faces the arc-shaped part, and the remaining part of the side face of the rotation axis does not face the arc-shaped part, the frame is placed on an opposite side of the rotation axis from the element part, and is parallel to the cable connecting surface of the element part when the element part is positioned at the middle of the scanning range, the other end of the relay cable is fixed to the frame in a direction parallel to the surface of the frame, and the relay cable is electrically connected to an outer portion of the housing part with the liquid sealed in the housing part in a fixed part between the relay cable and the frame.

2. The ultrasonic probe according to claim 1, wherein the relay cable passes through the frame with the liquid sealed in the housing part in the fixed part between the relay cable and the frame.

3. The ultrasonic probe according to claim 2, wherein the fixed part contains an adhesive for sealing the liquid in the housing part.

4. The ultrasonic probe according to claim 1, wherein the cross section of the relay cable perpendicular to the rotation axis has two arc-shaped parts positioned point-symmetrically about an assumed point and shaped similarly to each other.

5. The ultrasonic probe according to claim 1, wherein at least a part of the relay cable is structured as a laminate of plural flexible printed boards or plural flexible flat cables.

6. The ultrasonic probe according to claim 5, wherein the plural flexible printed boards or the plural flexible flat cables are laminated in a state being in contact with each other but not fixed.

7. The ultrasonic probe according to claim 5, wherein the flexible printed boards or the flexible flat cables have signal lines formed on the one sides and ground lines formed on the other sides.

8. The ultrasonic probe according to claim 7, wherein the element part includes an array element formed by arraying plural oscillators, and the flexible printed boards or the flexible flat cables have plural signal lines corresponding respectively to the oscillators.

9. The ultrasonic probe according to claim 8, wherein the plural oscillators are divided into plural groups, received signals of the oscillators are processed for each of the groups, the flexible printed boards or the flexible flat cables have plural signal lines corresponding respectively to the oscillators, and the signal lines are bound together for each of the groups.

10. The ultrasonic probe according to claim 1, wherein not all parts of a side face of the rotation axis face the arc-shaped part.

11. ultrasonic probe according to claim 1, wherein the two arc-shaped parts include a first arc-shaped part and a second arc-shaped part, the first arc-shaped part is located closer to the element part than the second arc-shaped part, and the rotation axis is located at the curvature center of the first arc-shaped part.

* * * * *